US009576862B2

(12) United States Patent
Murray et al.

(10) Patent No.: US 9,576,862 B2
(45) Date of Patent: Feb. 21, 2017

(54) OPTICAL ACOUSTIC SUBSTRATE ASSESSMENT SYSTEM AND METHOD

(71) Applicants: RUDOLPH TECHNOLOGIES, INC., Flanders, NJ (US); The Regents of University of Colorado, Denver, CO (US)

(72) Inventors: Todd Murray, Golden, CO (US); Manjusha Mehendale, Morristown, NJ (US); Michael Kotelyanskii, Chatham, NJ (US); Robin Mair, West Chicago, IL (US); Priya Mukundhan, Lake Hopatcong, NJ (US)

(73) Assignees: RUDOLPH TECHNOLOGIES, INC., Bloomington, MN (US); THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 14/776,953

(22) PCT Filed: Feb. 5, 2014

(86) PCT No.: PCT/US2014/014890
§ 371 (c)(1),
(2) Date: Sep. 15, 2015

(87) PCT Pub. No.: WO2014/149213
PCT Pub. Date: Sep. 25, 2014

(65) Prior Publication Data
US 2016/0043008 A1    Feb. 11, 2016

Related U.S. Application Data

(60) Provisional application No. 61/799,089, filed on Mar. 15, 2013, provisional application No. 61/799,448, filed on Mar. 15, 2013.

(51) Int. Cl.
H01L 21/00    (2006.01)
H01L 21/66    (2006.01)
(Continued)

(52) U.S. Cl.
CPC ............ *H01L 22/20* (2013.01); *G01N 21/1702* (2013.01); *G01N 21/41* (2013.01);
(Continued)

(58) Field of Classification Search
CPC .......... H01L 21/78; H01L 22/12; H01L 22/20; H01L 21/0231; H01L 22/00; H01L 22/10; G01N 21/1702; G01N 21/41; G01N 21/9501; G01N 29/04; G01N 29/2418; G01N 2021/8461; G01N 2201/06113; G01N 2291/011; G01N 2291/028; G01N 2291/0423; G01N 2291/0426; G01N 21/00
See application file for complete search history.

(56) References Cited

U.S. PATENT DOCUMENTS 6,795,198 B1    9/2004    Fuchs et al.
9,041,931 B2 *  5/2015    Colgan ............... G01N 29/041
                                                356/301
(Continued)

OTHER PUBLICATIONS

International Search Report for International Application No. PCT/US2014/014890, mailed May 27, 2014.

*Primary Examiner* — Thanh T Nguyen
(74) *Attorney, Agent, or Firm* — Merchant & Gould P.C.

(57) ABSTRACT

A system and method for identifying one or more characteristics of a structure formed into a substrate is herein disclosed. Surface and bulk acoustic waves are induced in the substrate and travel past a structure of interest where the acoustic waves are sensed. Information concerning one or more characteristics of the structure is encoded in the wave.

(Continued)

The encoded information is assessed to determine the characteristic of interest.

9 Claims, 14 Drawing Sheets

(51) Int. Cl.

| | | |
|---|---|---|
| *G01N 29/24* | (2006.01) | |
| *G01N 21/17* | (2006.01) | |
| *G01N 21/95* | (2006.01) | |
| *G01N 21/41* | (2006.01) | |
| *G01N 29/04* | (2006.01) | |
| *H01L 21/78* | (2006.01) | |
| *H01L 21/02* | (2006.01) | |
| *G01N 21/00* | (2006.01) | |
| *G01N 21/84* | (2006.01) | |

(52) U.S. Cl.
CPC ......... *G01N 21/9501* (2013.01); *G01N 29/04* (2013.01); *G01N 29/2418* (2013.01); *H01L 21/78* (2013.01); *H01L 22/12* (2013.01); *G01N 21/00* (2013.01); *G01N 2021/8461* (2013.01); *G01N 2201/06113* (2013.01); *G01N 2291/011* (2013.01); *G01N 2291/028* (2013.01); *G01N 2291/0423* (2013.01); *G01N 2291/0426* (2013.01); *H01L 21/0231* (2013.01); *H01L 22/00* (2013.01); *H01L 22/10* (2013.01)

(56) References Cited

U.S. PATENT DOCUMENTS

| | | | |
|---|---|---|---|
| 9,111,838 B2* | 8/2015 | Solin | H01L 27/14665 |
| 9,448,057 B2* | 9/2016 | Jiang | G01B 11/2441 |
| 2006/0021438 A1 | 2/2006 | Klein et al. | |
| 2006/0256916 A1 | 11/2006 | Kotelyanskii et al. | |
| 2011/0116084 A1 | 5/2011 | Lee et al. | |
| 2013/0052760 A1 | 2/2013 | Cho et al. | |

* cited by examiner

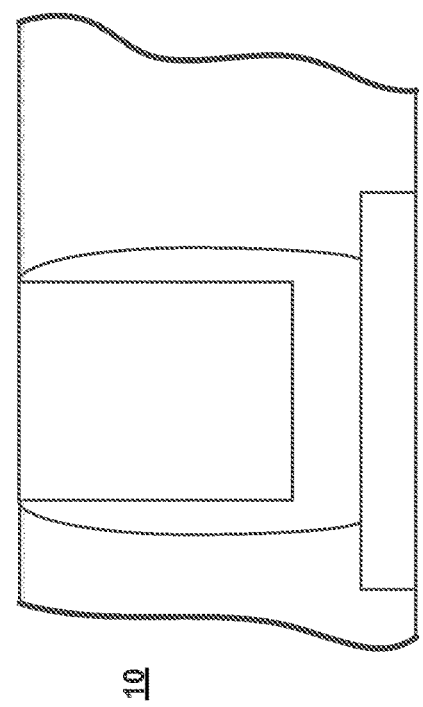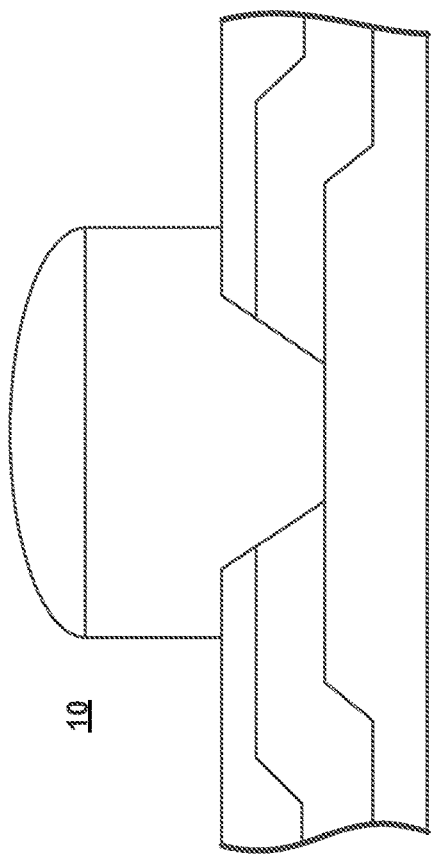
FIG. 2
FIG. 3

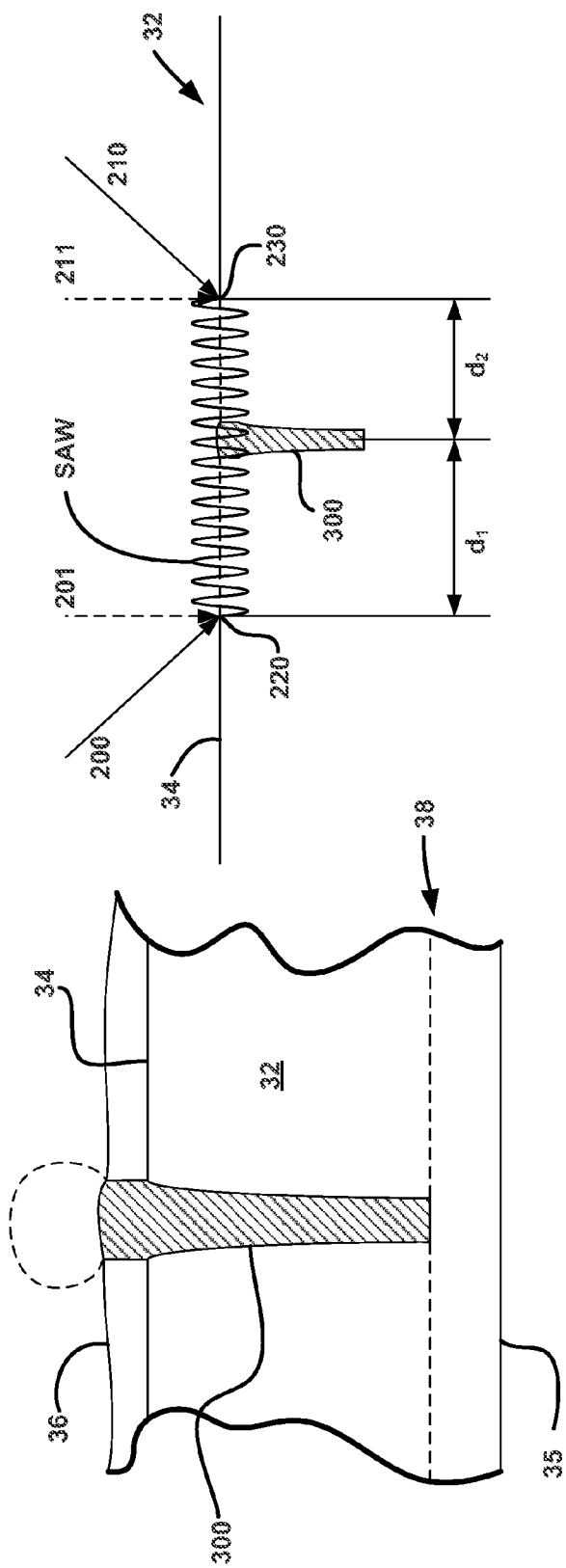

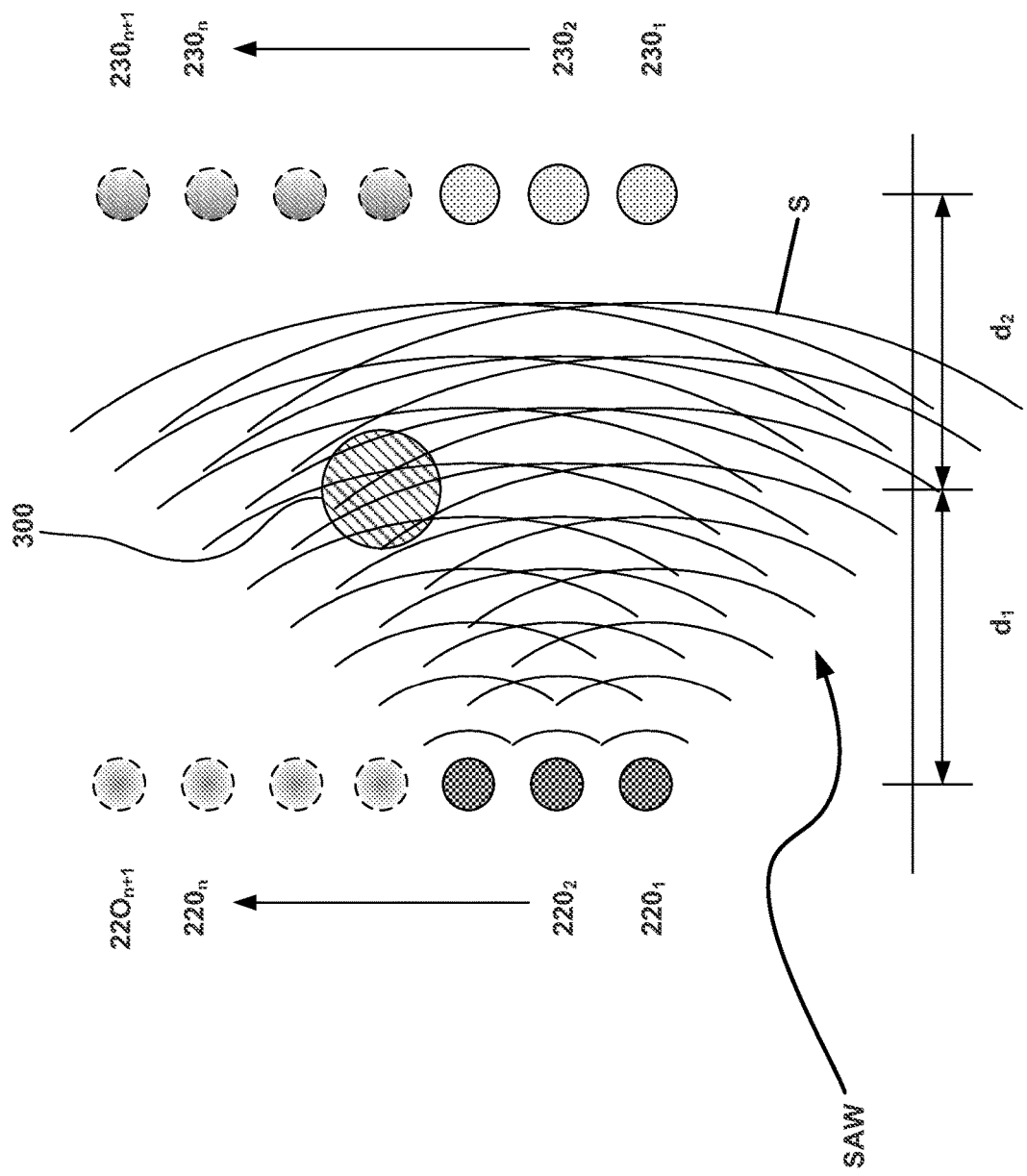

OPTICAL ACOUSTIC SUBSTRATE ASSESSMENT SYSTEM AND METHOD

This application is a National Stage Application of International Application No. PCT/US2014/014890, filed Feb. 5, 2014, which claims benefit of U.S. Provisional Application Ser. No. 61/799,089, filed Mar. 15, 2013, and U.S. Provisional Application Ser. No. 61/799,448, filed Mar. 15, 2013, the subject matter of which are incorporated by reference in their entirety.

TECHNICAL FIELD OF THE INVENTION

The present invention relates to an optical acoustic metrology system and method relating to the fabrication and testing of surface and subsurface structures formed into semiconductor substrates.

BACKGROUND OF THE INVENTION

Acoustic measuring systems operate by nondestructively penetrating solid materials to collect information regarding internal features, including defects such as cracks, delaminations and voids. Because of their ability to find and collect information nondestructively, acoustic microscopes for example have been used in the production of electronic components and assemblies for quality control, reliability, and failure analysis. There is a growing need in the field for further improvements in optical acoustic metrology systems and methods to both keep pace with, and drive advancements in, the semiconductor fabrication industry.

SUMMARY

The present invention may have many applications, but in one instance includes a system and method for assessing structures in substrates such as semiconductor wafers. One of such systems and methods of assessing structures in semiconductor wafers includes the step of inducing at least a surface acoustic wave at a first location of a surface of a substrate adjacent a structure that is formed at least partially transverse to the surface of the substrate. The length of time it takes for the surface acoustic wave to travel to a second location on the surface of the substrate is measured. The surface acoustic wave will at least partially interact with the structure formed in the substrate as it moves from the first to the second location. The inducement of surface acoustic waves in the surface of the substrate is repeated at multiple locations relative to the structure. Based upon at least the length of time data obtained from the measurements, a characteristic of the structure that is of interest may be determined. For example, the location of the structure, whether the structure is solid or hollow and/or whether the structure is continuous may be determined.

The present invention also relates to systems and methods for performing metrology on geographically delimited structures formed integral with a substrate using micro-fabrication techniques. Geographically delimited structures as used herein refers to three-dimensional structures that are the subject of the metrology and can include, for example, pillars, bumps, solder or metallic balls, bond pads and the like formed on a semiconductor wafer as part of a semiconductor device, such as a chip, interposer, multi-chip module or the like. These structures may be formed using lithography and other micro-fabrication techniques well known to those skilled in the art. The information obtained by the systems and methods according to the present disclosure is used in the manufacturing of these objects including, for example, for quality assurance purposes, for proving out design choices, and for controlling micro-fabrication processes used to form the object. It should be appreciated that the systems and methods disclosed herein can be employed in a wide variety of applications including applications well beyond the semiconductor fabrication industry.

BRIEF DESCRIPTION OF THE DRAWINGS

FIGS. 2-4 are cross-sectional representations of various semiconductor device structures to which the present disclosure may be addressed.

FIG. 5b is a graphic representing frequency domain data derived from the data shown in FIG. 5a.

FIG. 6 is a schematic representation of one type of via used in semiconductor devices.

FIG. 7 is a schematic elevational representation of the inducement and measurement of surface acoustic waves according to one embodiment of the present disclosure.

FIG. 8 is a schematic plan view of the inducement and measurement of surface acoustic waves according to an embodiment of the present disclosure.

DETAILED DESCRIPTION

Figure 1:
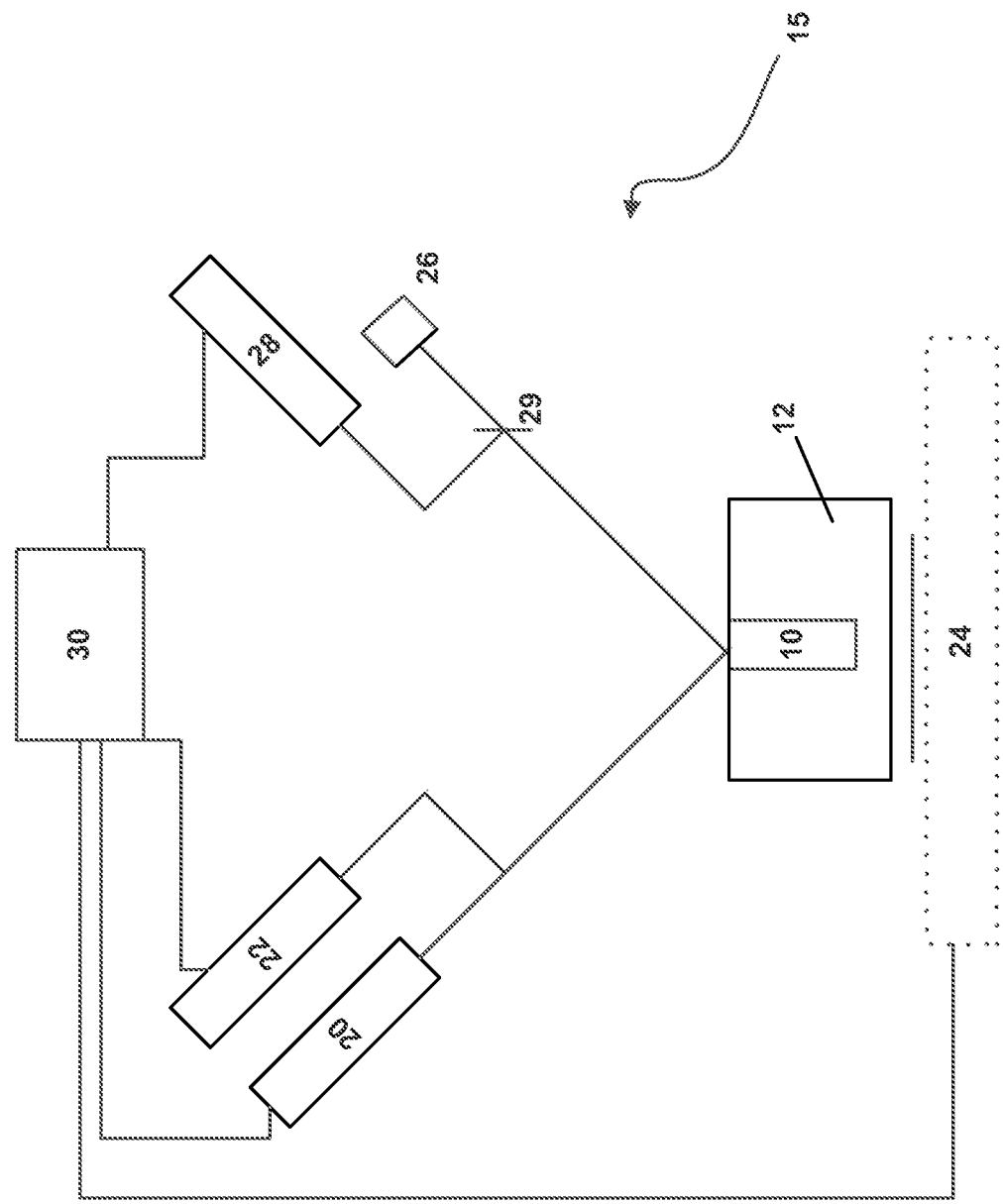
FIG. 1 is a schematic representation of one embodiment of opto-acoustic system in accordance with the principles of the present disclosure.

In the following detailed description of the invention, reference is made to the accompanying drawings that form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. The following detailed description is, therefore, not to be taken in a limiting sense, and the scope of the present invention is defined only by the appended claims and equivalents thereof.

Referring to FIG. 1, a schematic representation of an example opto-acoustic metrology system 15 that may carry out the method of the present invention is shown. In general this system includes a pump laser 20 (also referred to herein as a excitation laser); a probe laser 22 (also referred to herein as a detection laser); optics including lenses, filters, polarizers and the like (not shown) that direct radiation from the pump and probe lasers 20, 22 to an object 10; a mechatronic support 24 for a substrate/sample 12 of which object 10 is a part, the mechatronic support 24 being adapted to move the substrate 12 relative to the pump and probe lasers 20, 22; a beam dump 26 for capturing radiation from the pump laser returned from the object 10; a sensor 28 adapted to sense an intensity of radiation from the probe laser 22 that is returned from the object 10; and, a controller 30 coupled to the probe and pump lasers 20, 22, the mechatronic support 24, and the sensor 28.

It should be appreciated that the controller 30 may be a self-contained or distributed computing device capable of performing necessary computations, receiving and sending instructions or commands and of receiving, storing and sending information related to the metrology functions of the system.

Figure 13:
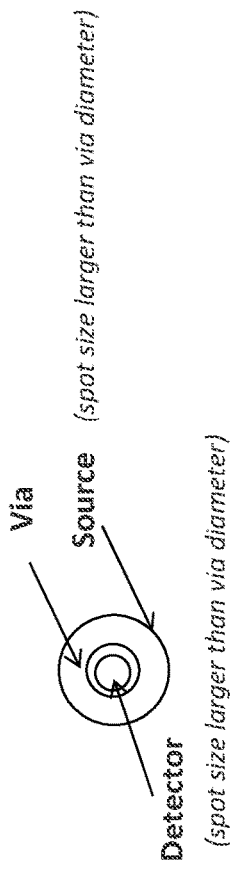
FIG. 13 is a schematic illustration of an exemplary detection (probe) and excitation (pump) laser configuration of the system of FIG. 11.

In the depicted embodiment the pump and probe lasers 20, 22 in the embodiment of the opto-acoustic system 15 shown in FIG. 1 can share at least a portion of an optical path to and from the object 10. For example, the lasers can have a number of different relative arrangements including a configuration wherein the paths are the same, partially overlapping, adjacent, or coaxial as shown in FIG. 13. In other embodiments, the pump and probe lasers 20, 22 and the beam dump 26 and sensor 28 do not share optical paths. Preferably, the pump and probe lasers 20, 22 may be controlled directly so as to obtain the necessary temporal spacing between the pulses of light directed to the object 10.

It should be appreciated that many optical configuration are possible. In some configurations the pump can be a? pulsed laser with a pulse width in the range of several hundred femtoseconds to several hundred nanoseconds and the probe beam is a continuous wave beam coupled to an interferometer or beam deflection system. For example, in systems wherein the probe is pulsed the system can employ a delay stage (not shown) for increasing or decreasing the length of the optical path between the laser and the object 10 associated therewith. The delay stage, where provided, would be controlled by controller 30 to obtain the necessary time delays in the light pulses incident on the object. Many other alternative configurations are also possible. On other embodiments, the system does not include a delay stage. It should be appreciated that the schematic illustration of FIG. 1 is not intended to be limiting, but rather depict one of a number of example configurations for the purpose of explaining the new features of the present disclosure.

In operation the opto-acoustic metrology system 15 directs a series of pulses of light from pump laser 20 to the object 10. These pulses of light are incident (i.e., at an angle which can be any angle between zero to 90 degrees including, for example, 45 degrees and 90 degrees) upon and at least partially absorbed by the object 10. The absorption of the light by the object causes a transient expansion in the material of the object 10. The expansion is short enough that it induces what is essentially an ultrasonic wave that passes down into the object 10 in much the way that sonar waves pass down into a body of water. Light reflected from the object 10 is passed into a beam dump 26, also commonly referred to as a "photon motel", which extinguishes or absorbs the pump radiation.

In addition to directing the operation of the pump laser 20, the controller 30 directs the operation of the probe laser 22. Probe laser 22 directs radiation in a series of light pulses onto the surface of the object 10 in a time sequence that is intended to intercept the return of the ultrasonic wave to the surface of the object. The interaction of the light pulses from the probe laser 22 with the surface of the object 10 as the ultrasonic waves return to its surface modifies the light pulses from the probe laser which are directed from the object 10 to the sensor 28 by means of beam splitter 29. The sensor 28 may be adapted to sense a change in the intensity of the probe beam of light caused by stress induced changes in the optical characteristics of the object due to transient stress waves passing through the system.

In a configuration where a continuous wave (CW) probe laser is used, an in-plane or out of plane displacement of the surface of the sample can be detected using interferometry. Alternatively, the change in surface tilt or change in surface curvature can be analyzed by detecting the beam deflection. Alternatively, or in addition to sensing changes in intensity, the sensor 28 may sense a deflection of the probe beam of light due to physical perturbations in the surface of the object 10 due to transient stress waves intersecting the surface of the object 10. The sensor 28, in one embodiment is a position sensitive device (PSD) that may sense both intensity and deflection.

As discussed above, in one embodiment the focused pump and probe beams are directed to the same spot on the object 10. In another embodiment, the pump and probe beams may be laterally offset from one another, the probe beam preferably being positioned on the object 10. The pump beam may be offset laterally from the probe beam and yet still on the object 10 or positioned adjacent to the object 10. Note that an offset may be achieved by using separate optical paths for the pump and probe beams or by using beams of different wavelengths that are passed through a glass plate that diffracts each beam differently. It may also be desirable to dither one or both of the pump and probe beams to avoid ablation or damage to the surface thereof.

The spot sizes of the pump and probe beams may vary based upon the particular application to which the method is put. The spot sizes of the respective beams may be similar or dissimilar. The spot size of the respective beams may, for example, range from around 100 microns to approximately the wavelength diffraction limit of the optical system used to carry out the optical acoustic metrology process, i.e., to less than 1 micron. The spot size of the laser can be in part based upon the size of the structure being measured, which will be discussed below in further detail with reference to FIGS. 13 and 14.

Figure 4:
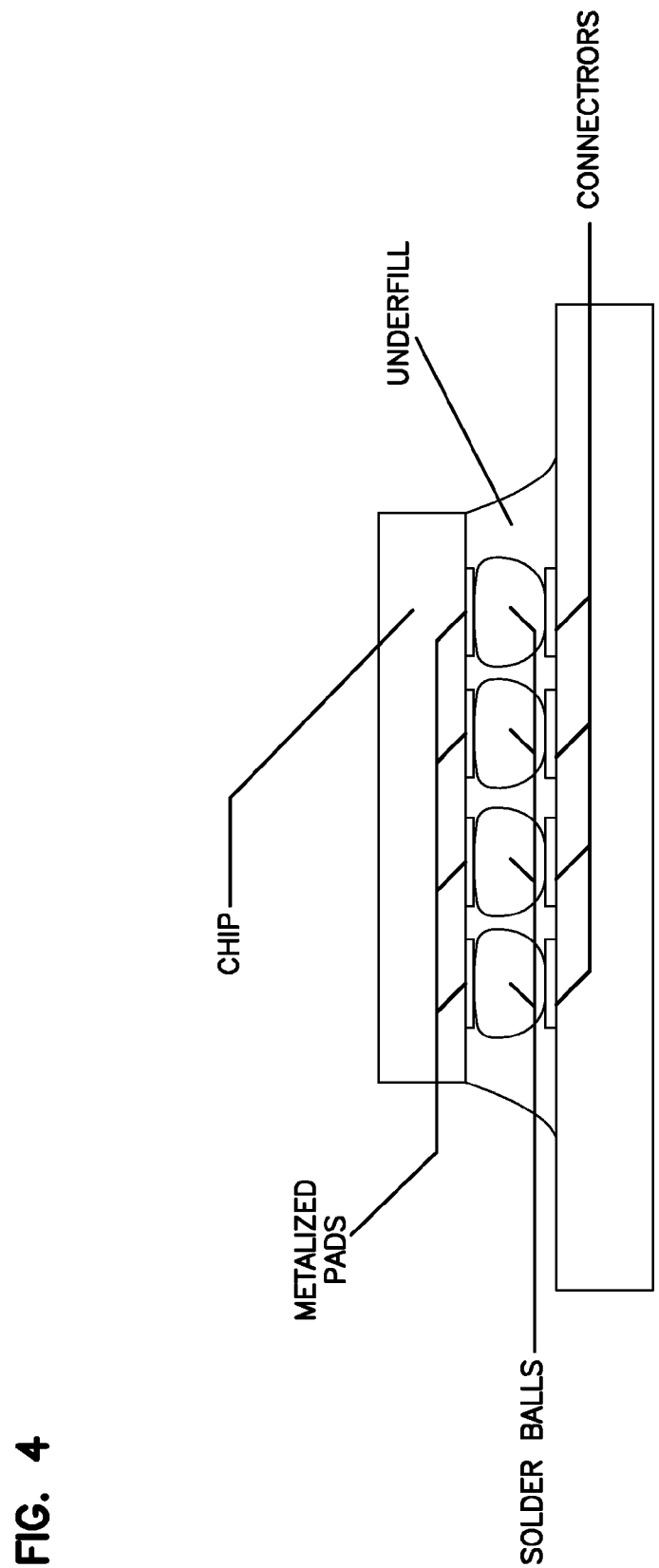

FIGS. 2-4 illustrate some exemplary objects that may be assessed using the present invention. The objects 10 illustrated in FIGS. 2-3 are commonly known as "pillars" in the semiconductor industry. Pillars are, along with solder or metallic balls or pads, structures for making electrical or thermal connections between semiconductor devices and substrates. FIG. 4 illustrates the use of solder balls to connect a semiconductor chip to underlying electronics in a configuration well known to those skilled in the art as a "flip chip" package. In the illustrated embodiment the focus of the inspection is not necessarily the integrity of the connections on a flip chip but rather the delimited structures associated with flip chip fabrication. As discussed above, it should be understood that the present disclosure may be used to assess pillars, balls, bumps, pads and other geographically delimited structures for making electrical and thermal connections between all manner of semiconductor devices and substrates. It should be appreciated that the structure and geometry that is the subject of the metrology can be as illustrated on the surface of the sample or under the surface of the sample (buried, embedded, etc.).

Figure 5B:
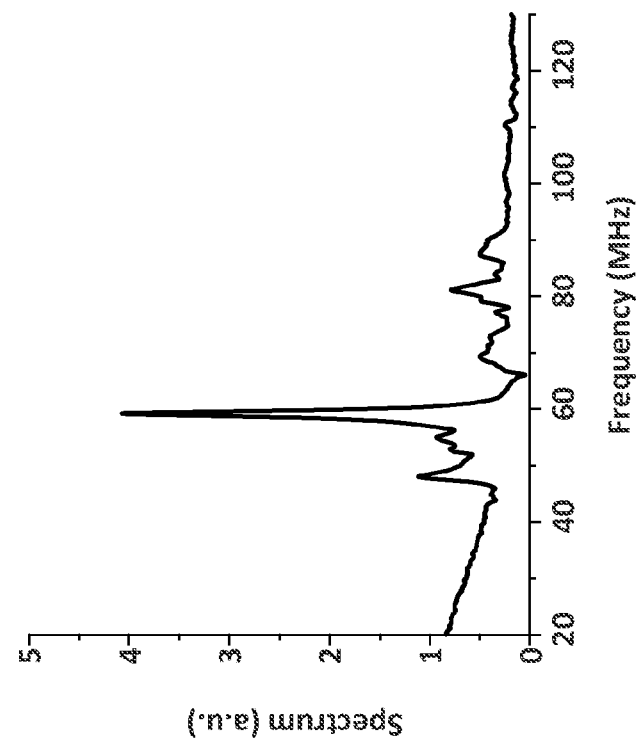
Figure 5A:
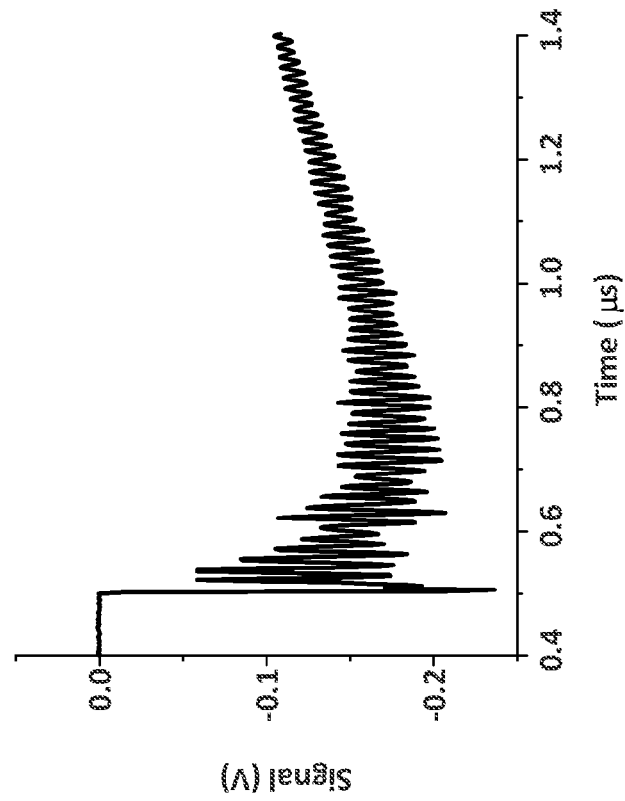
FIG. 5a is a graphic representing time domain data obtained from an opto-acoustic system such as that shown in FIG. 1.

Referring to FIG. 5a, example data obtained from an opto-acoustic metrology system 15 directed to a pillar having a layered structure of the type shown in FIGS. 2-3 is shown. Specifically, the pillar under assessment has an upper layer of SnAg beneath which are layers of Ni, Cu, and polyimide (PI) on a silicon wafer. The signal in FIG. 5a shows the intersection with the surface of the pillar/object 10 of acoustic/vibrational waves traveling within the pillar/object 10. The vertical axis is the measured signal in voltage that represents the deflection of a surface (surface deformation) that results for the induced acoustic wave at a particular location of a period of time.

Transforming the surface deformation time domain information represented in FIG. 5a to the frequency domain using a Fourier transform results in the data found in FIG. 5b. The peaks in the frequency can be correlated to various structural dimensions. For example, the large peak may be correlated to the diameter of the pillar in the sample. The exact location of the peak along the horizontal frequency axis can represent the magnitude of the diameter.

As can be seen, the multi-layer structure of the pillar exhibits multiple resonant frequency peaks. It should be appreciated that while in some instances there is a simple direct correlation between structures of interest (e.g., diameter, number of layers, unique embedded geometry, thicknesses of layers, etc.) and the frequency domain information shown in FIG. 5b, it is more often the case that object geometries are not so simply identified. Generally, computation or analytical vibrational analysis of nominal object geometries must be modeled to identify correlations between geometries and frequency domain information as illustrated. As an object 10 can vibrate in many different modes, models and databases of possible results are constructed to reflect those vibrational modes and their measurable results that may, in fact, be directly correlated with an actual geometry of the object 10.

In addition to the bulk waves that penetrate the substrate, the system of the present disclosure is capable of generating surface acoustic waves for metrology purposes. Surface acoustic waves are vibrations in a medium that propagate near the surface of the medium. Surface acoustic waves may be induced by means of piezoelectric actuators secured to the surface of the medium or by the thermoelastic effect in which a laser pulse rapidly heats a portion of the surface so as to create localized expansion of the medium. Surface acoustic waves moving through a medium typically assume a characteristic oscillatory pulse shape that may contain specific information about the mechanical and/or elastic properties of the medium or layer(s) through which the waves move. Decoding information about specific features of a structure or medium that may be obtained from data derived from the pulse shape of surface acoustic waves can be difficult however. In practice, the nominal structure of a given medium and variations thereof each set a unique stage from which characteristic information, if any, must be determined.

FIG. 6 illustrates schematically a through silicon via (TSV) 300, which is one type of via commonly used in semiconductor structures. Those skilled in the art will readily understand that this type of via is representational only and that the present invention may be applied to many different types of via. In addition, those skilled in the art will readily appreciate that the present invention may be applied to many types of 3D structures commonly found in current and planned semiconductor devices and/or packaging including, but not limited to, the ones shown in FIGS. 2-4 and identified elsewhere herein. It is noted that a given substrate may have one or more than one structure such as the illustrated via 300, and in some instances may have many thousands of such structures.

Via 300 is formed through an upper surface 34 and into the body of a substrate 32, in this case a silicon semiconductor substrate. Conductors and/or insulators that form the active portion 36 of an integrated circuit device are deposited onto the upper surface 34 of the substrate 32. Note that the active portion 36 may itself be formed of multiple discrete layers (not shown) using any one of a number of known lithographic techniques including, but not limited to, etching, deposition, masking, and develop. In some instances the upper, exposed surface of the via 300 will be used to form connections to other structures. This can be done by laying conductive traces (not shown) over the upper, exposed surface of the via 300 or, as shown, placing a solder bump or pillar in contact with the via 300. Note that in general, but not in all cases, bumps/pillars or other connections will be made at a stage in the fabrication process that is later than when the inspection techniques of the present invention are employed.

Figure 17:
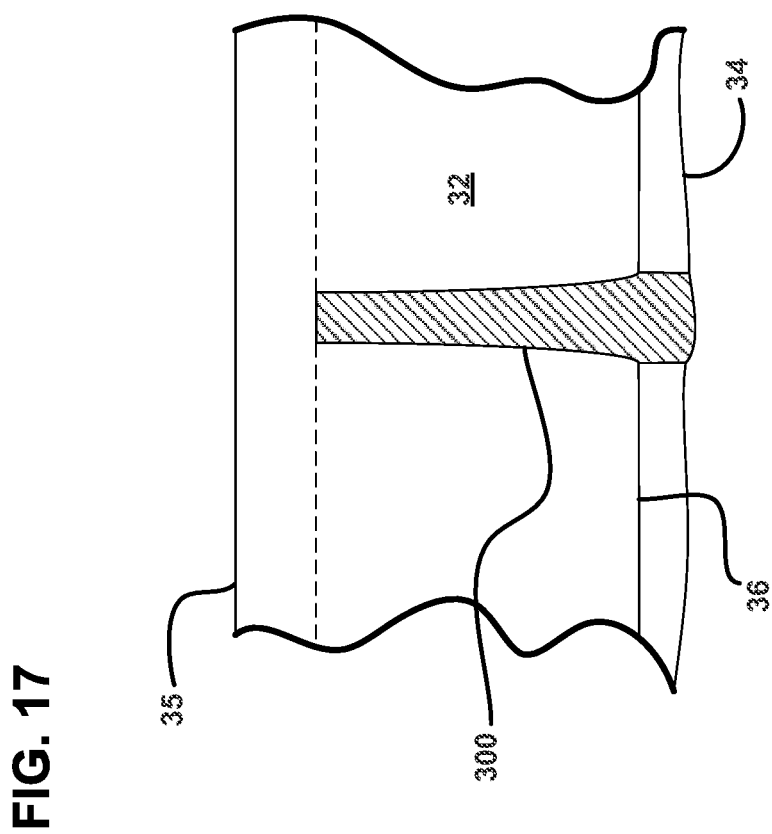
FIG. 17 is a schematic representation of an alternative inspection method according to the present disclosure.

In the embodiment shown in FIG. 6 via 300 terminates within the body of the substrate 32. Dashed line 38 indicates the position to which the substrate 32 will be ground or removed, thereby exposing the bottom surface of the via 300 for connection to other structures or integrated circuits. The systems and methods disclosed herein can be used in the microchip fabrication process. For example, prior to back grinding a wafer, the via can be inspected for void. If the metrology step identifies that a void exists in the via that renders the via defective, the costly and timely step of back grinding can be avoided. Therefore, according to one method of manufacturing, the back grinding occurs only if the via inspected is determined not to include voids that would render the via defective. The system and method can also be integrated into the fabrication process as a control to monitor production and aid in the upstream setup of processes. In other words, the system and method can be used to inspect structures such as vias to identify when the processes used to form the via have developed a problem as certain types of small voids are noticed or other unusual and undesirable structural changes begin to occur within the vias. Inspection of vias 300 and other 3D structures in a substrate 32 is a difficult proposition. Much of the active portion 36 of a substrate is opaque to optical imaging techniques. Some techniques utilize near infrared illumination and imaging techniques to view vias 300 from the reverse side 35 of the substrate 32 (see FIG. 17)?. Infrared imaging techniques are, however, subject to certain resolution and noise problems. The use of surface acoustic waves that travel in the active portion 36 of the substrate 32 or in the region of the substrate immediately adjacent the upper surface 34 of the substrate 32 avoids many of the drawbacks associated with imaging vias 300 and other structures.

FIG. 7 illustrates how surface acoustic waves are induced in a substrate 32 and how perturbations in surface acoustic waves can be measured. Radiation pulse 200 is incident upon the substrate 32 at an oblique angle or normal angle (201). The wavelength, polarization state, power, angle of incidence and at times the azimuthal angle of radiation pulse 200 are selected so as to permit a sufficient portion of the radiation pulse 200 to be absorbed by the substrate 32 as heat. The heating of the substrate 32 at a specified location causes a sudden expansion of the substrate 32 that induces an ultrasonic wave in the material of the substrate 32. This ultrasonic wave emanates more or less spherically from the point of incidence 220 into the substrate 32. The portion of the ultrasonic wave that moves into the substrate perpendicular/downwardly into the surface 34 of the substrate 32 is referred to as a bulk wave (see FIG. 11). The portion of the ultrasonic wave that passes along the surface 34 of the substrate 32 is referred to as a surface acoustic wave or SAW. Note that the radiation pulse is often a laser beam and may be referred to as a pump beam.

The SAW that emanates from the point of incidence 220 has components that travel along the surface of the substrate 32, past a via 300, to a second point of incidence 230 at which a second radiation 210 (pulse or continuous wave) is incident upon the surface 34 of the substrate 32. Radiation pulse 210 is used to sense changes in the reflectivity and shape (deformation) of the substrate 32 due to the SAW as a function of time. In one embodiment, changes in reflectivity and shape are recorded as a function of the time it takes for a SAW to propagate from position 220 to position 230, i.e., a distance equal to the sum of distances $d_1$ and $d_2$ illustrated in FIGS. 7 and 8.

FIG. 8 illustrates one manner of obtaining SAW data that encodes at least location information about a 3D structure formed in a substrate. As will be appreciated, substrates 32 may have one, many, or even thousands of structures 300 that may require inspection or assessment. Accordingly, it is desirable to induce the radiation 200, 210 past multiple structures or vias 300. In one embodiment, a user may make a simple spot check of structures 300 of a substrate 32. In this embodiment, only a single structure 300 or relatively few structures 300 (e.g. 5-25 vias) are assessed on a substrate. In another embodiment a significant portion of accessible structures are assessed. A significant portion in this context may constitute between 10% and 75% of all structures or vias 300 on a substrate 32. In some other embodiments, substantially all (75%-100%) accessible structures or vias 300 on a substrate are assessed. Note that a structure or via 300 is "accessible" when at least a portion thereof is located within the portion of the substrate 32 through which the surface acoustic waves propagate. A structure or via 300 is not accessible if surface acoustic waves cannot interact with the structure or via 300.

FIG. 8 illustrates one embodiment of the present invention. A radiation pulse, otherwise referred to as a pump beam, is incident upon the surface of a substrate 32 at an incident position 220. The absorption of at least a portion of the radiant energy of the pump beam by the substrate 32 induces a surface acoustic wave (lines S) in the surface of the substrate 32. While the SAW will radiate in all directions from the incident point 220, the SAW will propagate toward a second incident point 230. As will be appreciated, the SAW propagating through the substrate 32 will also pass through the structure or via 300, thereby encoding information relating to the form or nature into the SAW. The SAW then continues on to the second incident point 230 where a second radiation pulse (not shown) is incident upon the substrate 32. The second radiation pulse, also known as a probe beam, is used to obtain data from the SAW that includes the information relating to the form or nature of the structure or via 300. Various methods for performing this measuring are described hereinbelow. Other techniques will be readily understood to those skilled in the art.

In one embodiment the pump/probe cycle is repeated multiple times for each set of incident points 220, 230. In this way, the multiple data points may be summed, averaged, or otherwise combined to provide useful data. It should be understood however, that this cycle may be performed any number of times required to obtain useful data, including a single repetition. The data obtained by means of the probe beam may be encoded as a function of XY position of the via and/or the incident points 220, 230 or both. Further, the time it takes for the SAW to move from the first incident point 220 to the second incident point 230, past the structure or via 300, may be measured or determined as a function of the position of the incident points 220, 230 with respect to the structure or via 300.

In one embodiment, the substrate 32 is moved relative to the source of the radiation pulses 200, 210 so as to position their incident points 220, 230 as shown in FIG. 7 and at $220_1$ and $230_1$ as shown in FIG. 8. As described above, any needful number of measurement cycles may be undertaken at positions $220_1$ and $230_1$, including a single measurement cycle. Once measurement at positions is complete, the substrate and/or the source of the radiation pulses 200, 210 are moved relative to one another so as to position the points of incidence of the radiation pulses at positions $220_2$ and $230_2$ seen in FIG. 8. Again, a needful number of measurement cycles are undertaken, including possibly only a single cycle. Thereafter, the substrate and/or the source of the radiation pulses are repeatedly moved to the locations $220_n$, $230_n$, at which locations one or more measurement cycles are conducted. Note that in some embodiments the movement between the n incident positions is conducted in a stop/start manner, i.e., the substrate and the source of the radiation pulses are moved relative to one another to the desired position after which they are maintained stationary with respect to one another until all necessary measurement cycles are completed. While relatively slow, the stop/start method of addressing the radiation pulses to the substrate allows for a high degree of optical and physical control.

It should be appreciated that the above-described methods as well as other metrology methods disclosed herein can be applied to both sides of a sample. For example, with reference to FIG. 7, it should be appreciated the methods disclosed herein could be used on an underside of a wafer. In such an embodiment, the structures of interest of the sample (e.g., vias) can be inspected for voids by inducing acoustic waves (surface and bulk) into the bottom surface of the wafer as opposed to, or in addition to, inducing optical acoustic waves onto the top surface of the wafer/semiconductor substrate. One method of such metrology would involve inverting the wafer and another method would involve reorientation/redirection of the pump and probe laser beams onto the bottom surface of the sample (e.g., wafer).

Figure 9A:
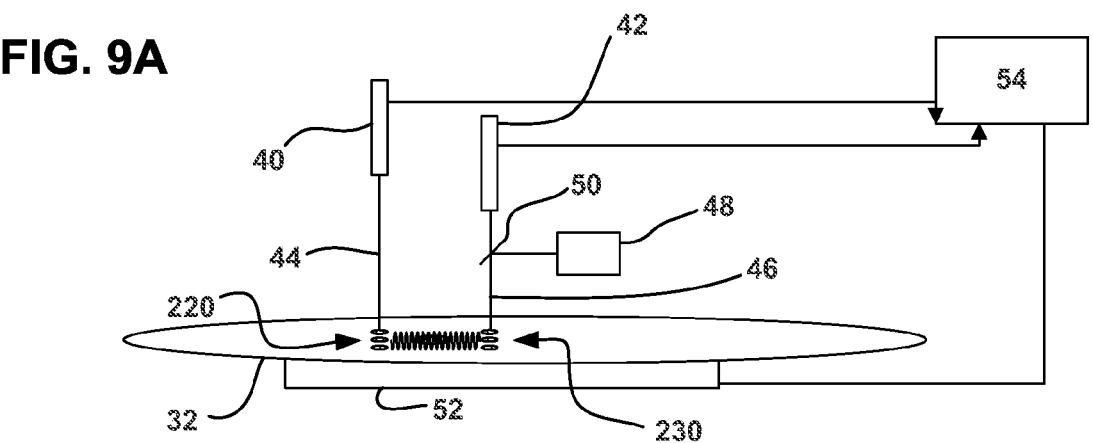
FIGS. 9a-9c are schematic representations of selected optical systems useful for carrying out various embodiments of the present disclosure.

Many optical arrangements in addition to the ones described above may be used to carry out the various embodiments of the present invention. For example, FIG. 9a illustrates an embodiment of the present invention in which separate lasers 40, 42 provide pump and probe beams of radiation 44, 46, respectively. While the lasers 40, 42 are shown in a normal incidence orientation, it will be appreciated that oblique incidence orientations are inherently described by this arrangement. Pump beam 44 from laser 40 is incident upon the substrate 32 at one or more points of incidence 220 to induce surface acoustic waves SAW in the substrate. Probe beam 46 from laser 42 is incident upon the substrate 32 at one or more second points of incidence 230 to sense information related to the surface acoustic wave and the structure of the substrate 32. In the embodiment illustrated in FIG. 9*a*, a sensor 48 is coupled into the optical path of the laser 42 via beam splitter 50. The sensor 48 may be a position sensitive detector (PSD) or the like, and may sense any useful characteristic such as deflection of the substrate 32 or changes in the reflectivity or other optical properties of the substrate. Note that sensor 48 may measure the characteristics of the substrate 32 as absolute values or as functions of other data such as, for example, time.

The lasers 40, 42, sensor 48 and a stage 52 upon which the substrate 32 is supported are controlled by a controller 54. The controller 54 positions the substrate 32 so as to ensure that each of the lasers 40, 42 are incident at the appropriate points 220, 230. The controller 54 also controls the operation of the lasers 40, 42 to ensure that the lasers operate in the manner necessary to induce and measure surface acoustic waves in the substrate 32 in both an absolute value sense and as a function of time. Accordingly, the embodiment shown in FIG. 9*a* may determine, among other things, how long it takes a surface acoustic wave to travel from a first point of incidence 220 to a second point of incidence 230 as a function of the position of the substrate relative to the position of a structure 300. Note that the position of the substrate 32 relative to the stage 52 is determined by means of a calibration that may be carried out using an alignment system (not shown) that includes illumination, a camera or sensor, and a means for processing images/data captured from the camera or sensor to determine a relative position of the stage 52 and the substrate 32. In some instances, the laser 42 and sensor 48 may be used to determine a position of the substrate relative to the stage. In any case, the stage 52 has electronic or optical encoders (not shown) that provide accurate position information for the substrate 32 at any given time.

Figure 9B:
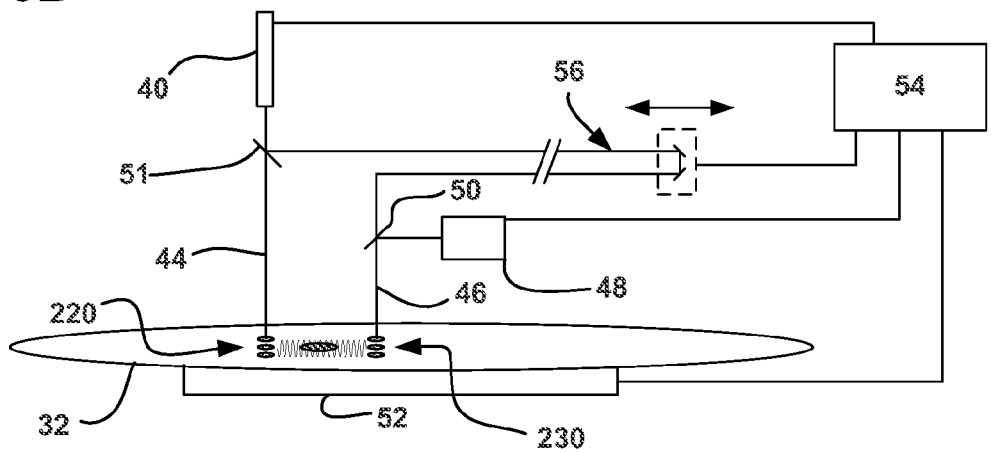

FIG. 9*b* illustrates an embodiment similar to that shown in FIG. 9*a*, the primary difference being that the latter utilizes a single laser 40 to provide radiation pulses to both the first and second points of incidence 220, 230. A beam splitter 51 positioned in the optical path of radiation emitted from laser 40 divides the radiation into two pulses: a pump pulse 44 and a probe pulse 46. The first pulse is incident on the substrate 32 at one of points of incidence 220. The second pulse passes through a delay stage 56 that modifies the path length traveled by the second pulse and by doing so, modifies the time delay at which the second pulse is incident at one of the second points of incidence 230 with respect to the incidence of the first pulse at point of incidence 220. Light returned from points of incidence 230 is passed to a sensor 48 that measures one or more characteristics of the substrate 32 to identify information encoded in surface acoustic waves passing between points 220 and 230.

Figure 9C:
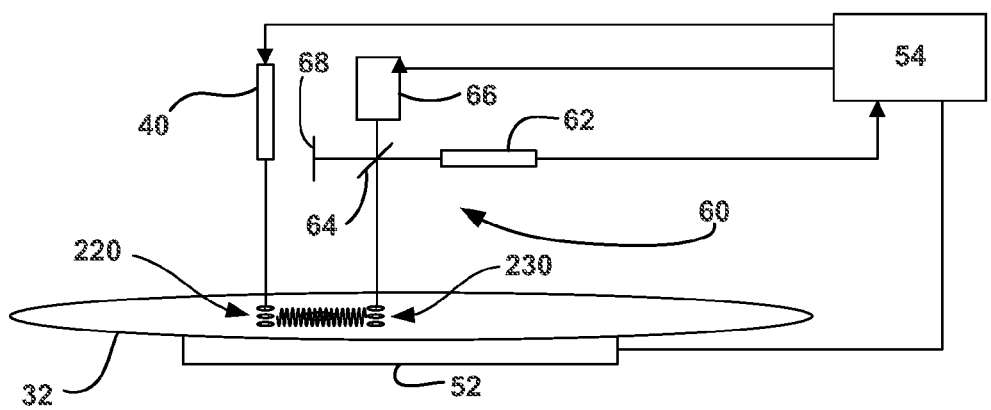

FIG. 9*c* illustrates yet another embodiment in which an interferometer 60 is utilized in lieu of a position sensitive detector to determine characteristics of a substrate 32. In this embodiment, a laser 62 passes through a beam splitter 64 which splits a beam between a first portion that is incident upon substrate 32 at point 230 and a second portion incident upon reference mirror 68. Light returned from the substrate 32 and the reference mirror 68 are combined by splitter 64 and returned to sensor 66, which may be an imaging device such as a camera or a point sensor such as a photo diode. Those of skill in the art will recognize this configuration as a Michelson interferometer. Other types of interferometers may also be of use.

Figure 10:
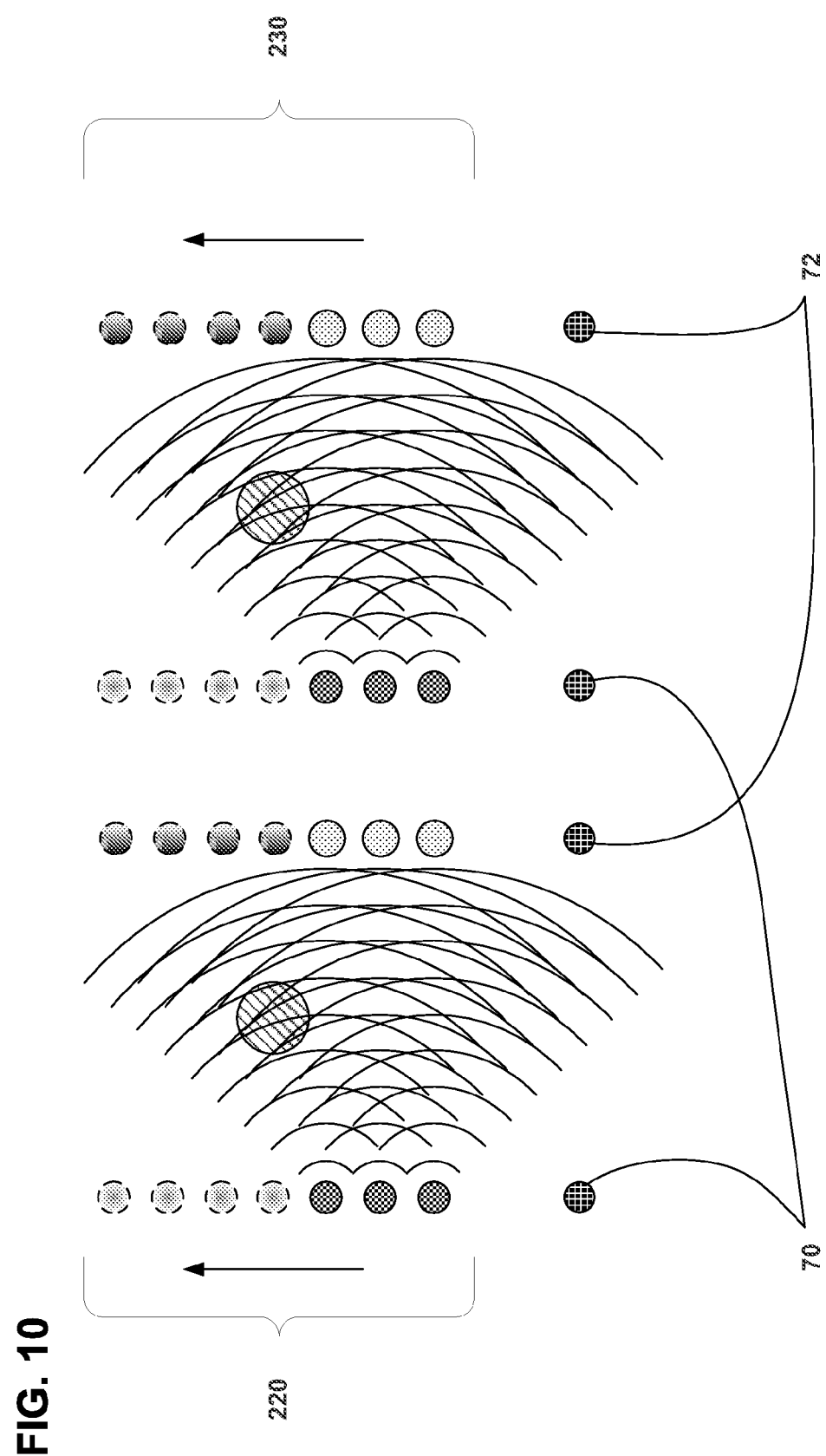
FIG. 10 is a schematic representation of multiple structures of a substrate being assessed simultaneously.

FIG. 10 illustrates an alternative optical arrangement in which a single laser beam is split into multiple pump beams 70. A single laser beam, derived from the same source as the pump beams 70 or from a distinct source, may likewise be divided or split into multiple probe beams 72. In this embodiment, the multiple probe and pump beams 72, 70 may be arranged to address multiple first and second points of incidence as shown. Optical devices such as an acousto-optic modulator or an electro-optic modulator may be used to split a single beam into multiple, independent beams. Other such arrangements are well known to those skilled in the art.

Those skilled in the art will also recognize that for purposes of clarity, certain optical elements commonly used in optical systems of the type described herein have been omitted. Some such optical elements include, but are not limited to: lenses, beam turning elements, fiber optic devices, beam mixers, polarizers, analyzers, band pass filters, stops, and the like.

As the systems and methods of the present disclosure are used to determine and identify characteristics of structures 300 of a substrate 32 on a repeated basis, it is desirable for the controller 54 to record a series of instructions for the operation of the present invention that permit for easy automation of the process. Such lists of instructions are often referred to as a "recipe." A recipe may be a list of text or binary inputs that may be read and implemented by the controller to carry out the determination of substrate characteristics. The recipe may include not only simple instructions, but also generic information about the substrates 32 that allow the controller 54 to perform as intended. Examples of data that may be included in the substrate are the size and shape of structures 300 as well as the location of sub-units of the substrate, e.g., the location of semiconductor devices on a wafer. Further, the recipe may include the nominal locations of all structures found on a substrate or a subset thereof.

In one embodiment, the controller directs the stage 52 to position the substrate 32 such that radiation beams may be incident upon points 220 and 230 as described above. In this embodiment, the substrate 32 is moved in a stop/start fashion, serially positioning the substrate 32 in a desired location and then dwelling at that location long enough for extraneous vibration to be damped out, for optical elements to be focused at the points 220, and 230, and for data concerning characteristics of the structures 300 to be captured. Multiple data gathering cycles may be undertaken during each stationary period in this manner.

In another embodiment, the controller 54 directs the stage 52 to move continuously so as to continually shift the points of incidence 220, 230 past the incident radiation beams. Where the continuous movement of the substrate 32 is sufficiently slow as compared to the pump/probe data collection process, one may consider each data gathering cycle (each pump/probe cycle) to have been conducted at an individual spot whose location is the center of the path that has been scanned during any given period. In this embodiment, all structures 300 on a substrate 32 may be scanned. Often this is done by establishing a boustrophedon path that sequentially brings all structures that are to be scanned to their desired location. Following a path of this type allows for rapid assessment of the substrate. In other embodiments, the boustrophedon path is used, but rather than inspecting or assessing all structures 300, only selected ones are addressed. In yet another embodiment, the stage 52 moves the substrate 32 along a path fit to the location of selected structures 300 on the substrate 32. This path may be a spline or a combination of linear and arcuate path sections. This mode of moving a substrate to address a sensor to selected locations is often referred to as a "drunkard's walk" path, though to be certain, the locations to be visited may or may not be chosen randomly.

In another embodiment, the optical system which carries out the pump/probe data gathering cycle is provided with optical mechanisms that allow the pump and/or probe beams incident upon points 220, 230 to be moved rapidly, i.e., dithered, to avoid imparting too much heat to any given location. In this case, one will consider the points 220, 230 to be the center of a region over which the beams are dithered. Data generated and collected by this arrangement are assigned to the center location defined by points 220, 230. This dithering technique may be used regardless of whether the substrate 32 and stage 52 move continuously or discontinuously.

In yet another embodiment, the optical mechanisms used for dithering a beam over a particular area or region of a substrate 32 may be used to maintain a pump/probe beam on a selected one of points 220, 230 as the substrate is scanned past the source of the pump/probe beam.

As indicated above, surface acoustic waves passing through and/or around structures such as vias formed into a substrate have encoded therein certain information that may be parsed to provide insight into the nature of the structure. Before data acquisition can begin however, it is first necessary to determine locations for the points of incidence of the pump and probe beams, respectively. While there exists a range of locations for each of these points of incidence, the key is to ensure that the first point of incidence 220 is close enough to the second point of incidence 230 to get a clear signal. As surface acoustic waves travel away from the source that induced them, the strength of the surface acoustic wave at any point away from the point at which it is initiated decays as $d^{-1/2}$, where d is the propagation distance. Accordingly, it is necessary to get the points 220, 230 close enough together to ensure that sufficient signal strength is achieved. At the same time, however, there is a desire to ensure that there is sufficient distance between the points at which pump and probe are carried out to span the structures that are of interest.

Figure 11:
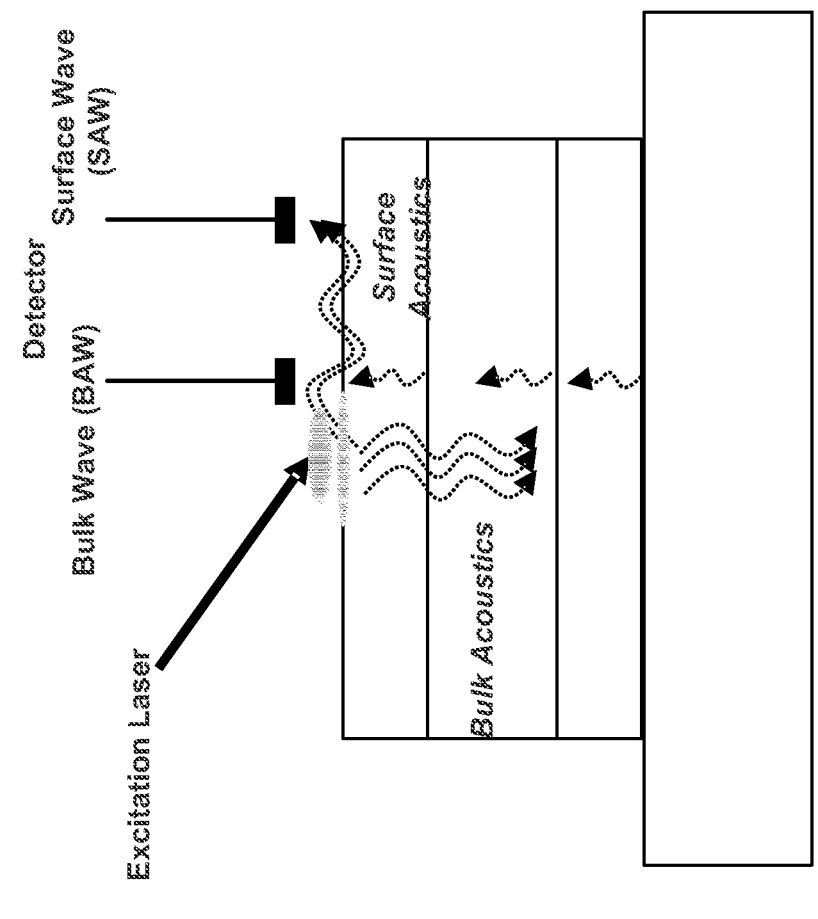
FIG. 11 is a schematic illustration of an embodiment of a system according to the present disclosure in operation that employs a combination of bulk acoustic wave detectors and surface acoustic wave detectors.

Referring to FIG. 11, a schematic illustration of a system and method that include both bulk wave (BAW) detection and surface wave (SAW) detection is shown. In the depicted embodiment a focused excitation laser is used to generate a bulk acoustic wave that travels downwardly into the substrate and bounces back upwardly towards the bulk wave detector. In the depicted embodiment, a focused optical probes coupled to a Michelson interferometer is configured to detect both the bulk waves and the surface waves induced in the sample. The probe beam in the depicted embodiment is configured to be physically separate from the pump beam so that they can be focused at different physical location on the sample under inspection. It should be appreciated that many other configurations are also possible including, for example, configuration that employ multiple focused optical probes.

In the depicted embodiment the excitation laser pulses for several hundred femtoseconds to several hundred nanoseconds to generate acoustics of the order of one megahertz to several hundred megahertz (e.g., 1-200 MHz). This relatively low frequency enables the system to measure structures buried or embedded relatively deep within the sample. For example, the system of the present disclosure in some embodiments is configured to detect voids and other internal defects in vias that are as deep as 300 microns below the surface of the sample (e.g., 0-75 micros, 0-50 microns, 0-300 microns, 50-300 microns, 100-300 microns, etc.). The system of the present disclosure can penetrate and measure samples and provide information about bumps, pads, pillars and other covered, buried, and embedded structures that are otherwise very difficult or even impossible to ascertain in a non-destructive manner. The pulse frequency in certain embodiments is sufficiently low to avoid the need to employ a delay stage for data collection. In some embodiments, the data is collected using a photo diode sensor alone (no delay stage). It should, however, be appreciated that in other embodiments, a delay stage may be employed as well (e.g., FIG. 9b).

In the depicted embodiment, the material response to the induced acoustic energy over a period of time is used to ascertain the geometry of structures in the samples. These material responses (e.g., surface deformations measured in voltage) correlate to, for example, via geometry and other material properties. In particular, the arrival times of the various modes in time domain can be, for example, used to provide qualitative information about the presence of absence of voids in vias.

Figure 12:
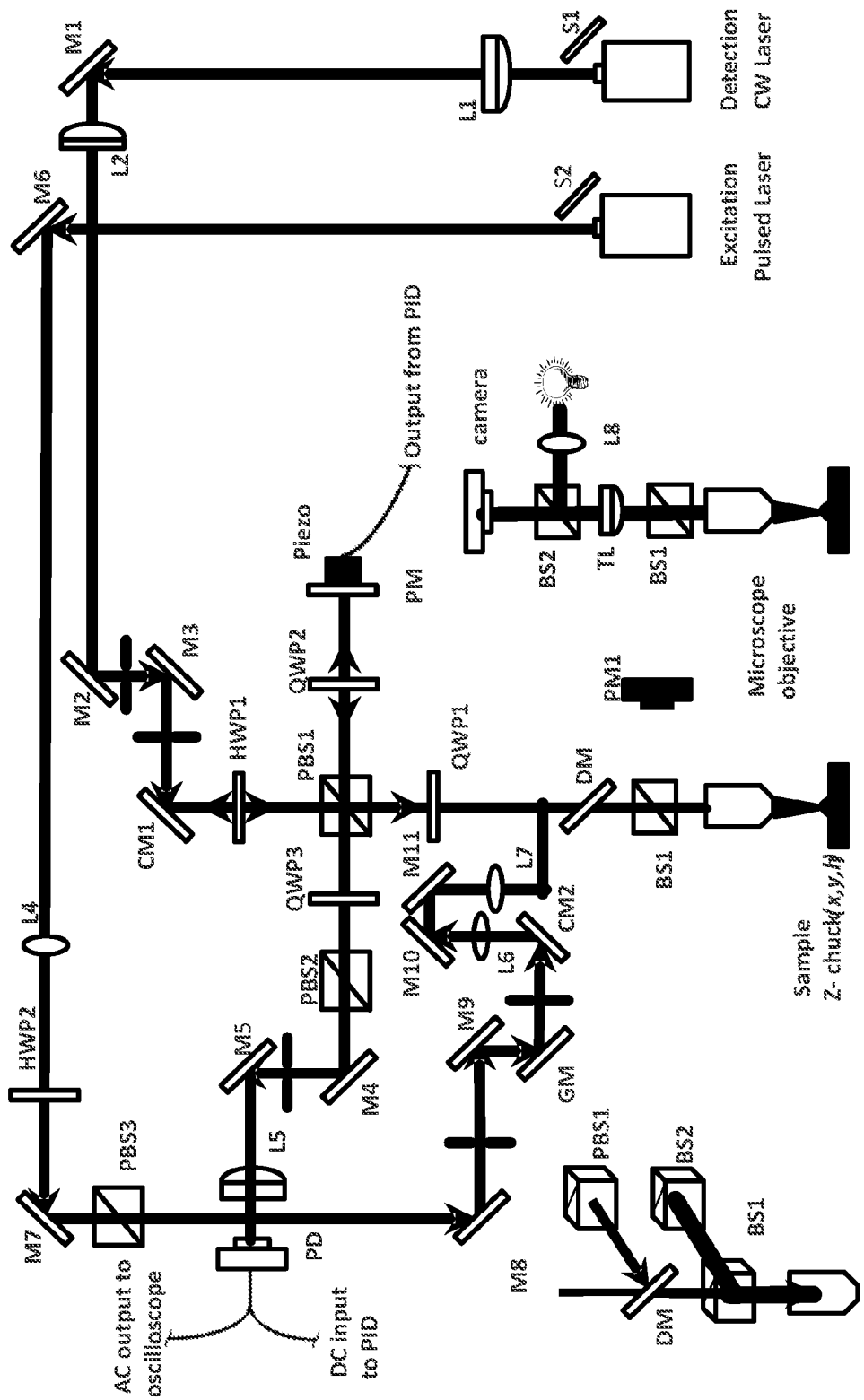
FIG. 12 is a schematic illustration of certain hardware components of the system of FIG. 11.

Referring to FIG. 12, an example optical schematic is shown. In the depicted embodiment an excitation pulsed laser directs a laser beam through a series of mirrors M6, M7, M8, M9, GM, CM2, M10, M11 and lenses L4, L6, L7 and other optical components a half wave plate HWP2, a polarizing beamsplitter PBS3, a non-polarizing beamsplitter BS1 to the sample located on the chuck. The excitation laser beam can alternatively be directed through lens L5, mirrors M5, M4, and a polarizing beam splitter PBS2 and a quarter wave plate QWP3. A detection laser directs a laser beam to through a series of mirrors M1, M2, M3, CM1 and lenses L2 and other optical components a half wave plate HWP1, a polarizing beamsplitter PBS1, a quarter wave plate QWP1, a dichroic mirror DM, and a non-polarizing beamsplitter BS1 to the sample located on the chuck. In the depicted embodiment, the system further includes a subsystem including a dichroic mirror DM a polarizing beam splitter PBS1, a non-polarizing beamsplitter BS1, and a non-polarizing beamsplitter BS2 and a subsystem including a camera, a non-polarizing beamsplitter BS2, lense L8, tube lense TL, a non-polarizing beamsplitter BS1.

Figure 14:
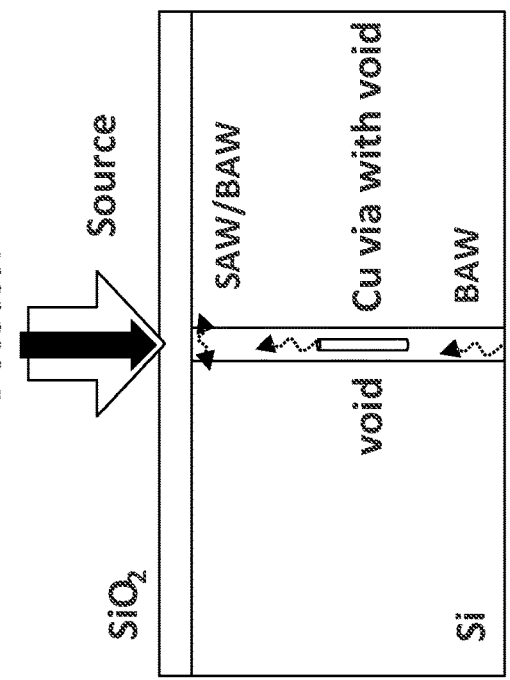
FIG. 14 is a schematic illustration of the laser configuration of FIG. 13 used to detect the presence of an internal defect in a sample.

Referring to FIGS. 13 and 14, the pump and probe beams are positioned directly above the via under inspection. In particular, in the depicted embodiment the detection laser beam is coaxially position within the excitation laser beam such that they overlap. In the depicted embodiment, the diameter of the excitation laser is sufficiently large to cover the via, whereas the diameter of the detection laser (probe beam) is smaller but also sufficiently large to cover the projection of the via. In the depicted embodiment, a single measurement can be performed to detect both the bulk and surface acoustic waves. The excitation laser induces an acoustic wave over the entire top surface of the via, and simultaneously (or sequentially) the detector probes for the bulk and surface wave response from the via. The above embodiment illustrates that the pump and probe beams can be arranged and configured based in part on the geometry of the structures that are the subject of the measurement. It should be appreciated that many alternative configurations are also possible. For example, in an alternative configuration the pump and probe beams could both have diameters that are smaller than the diameter of the via.

Figure 15:
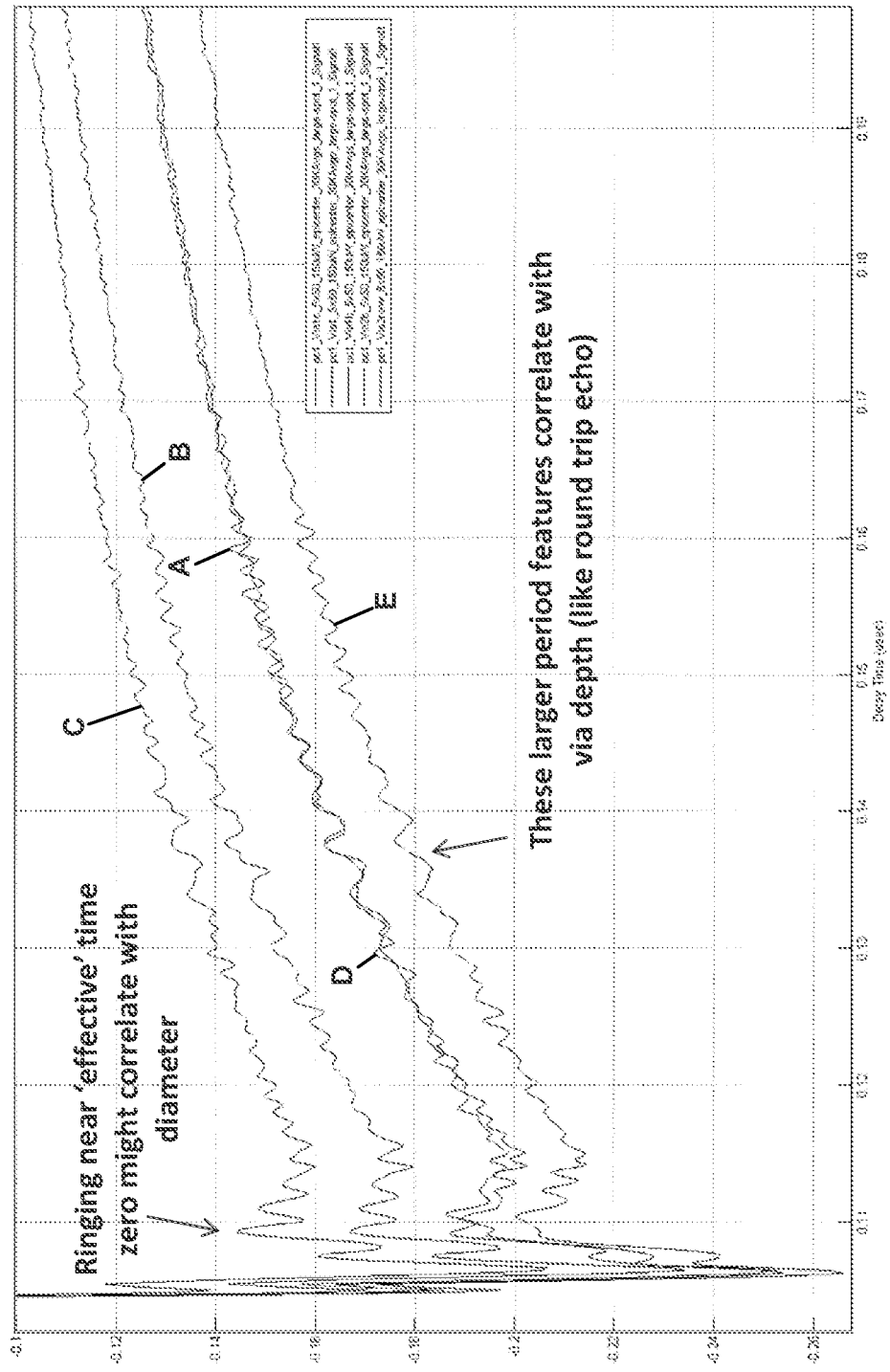
FIG. 15 is a graph of the data collected from the detection laser correlated to the diameter of a via and depth of a via.
Figure 16:
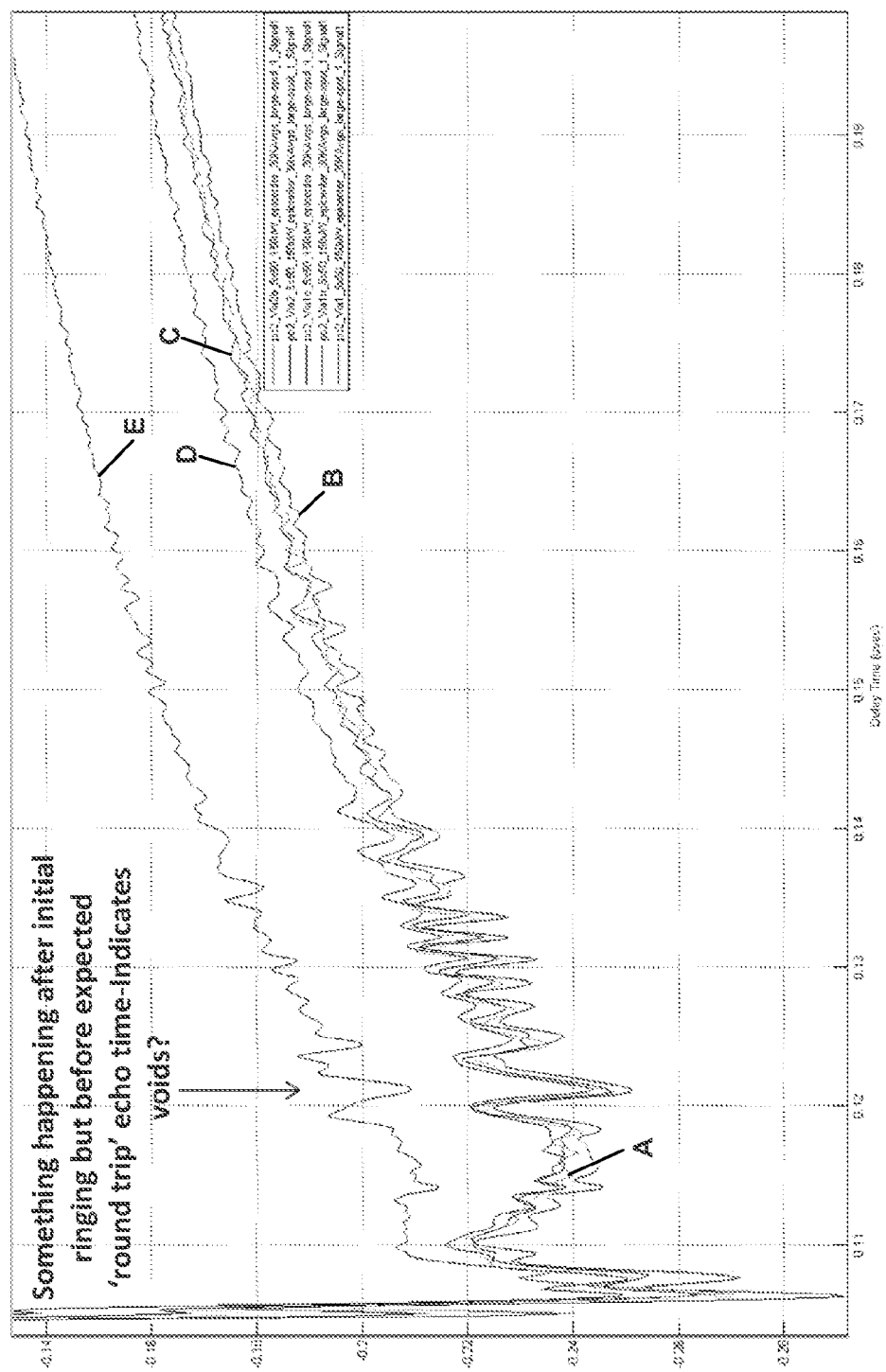
FIG. 16 is a graph of the data collected from the detection laser that is indicative of a void in a via.

Referring to FIGS. 15 and 16, the detector (probe laser) receives the return wave data that has encoded therein information regarding a void in the Cu via. For example, the data collected in terms of the time that it takes the bulk wave to return (i.e., echo time) can indicate that a void exists at a particular geographic location. The existence of a void can be correlated to an abnormality in the response to the acoustic energy as compared to the responses returned from samples that are known to not include such voids.

Additional and more specific information can be gathered regarding the structures under examination by further examining the return waves' frequency and return times. For example, the diameter of the via/void in the via and the depth of the via/void in the via can be ascertained.

As discussed above, deviations from the normal common response can indicate structures that are not normal. Structural abnormalities such as voids that can render the structure (e.g., via or pillar) and the substrate of which it is a part of (e.g., the die on the wafer) defective. In other words, vias without voids are measured, and the echo pattern comprising part of the signal at and around the delay times where the reflected wave arrives to the surface are "cut-out" and saved as the "template" signal vector. During metrology, new measurement signals are scanned with the template in search of the maximum of the correlation coefficient $C(t_m)$. If maximum of $C(t_m)$ occurs earlier than the expected return time from the bottom of the via, or earlier than it is observed from the known void-free via, the via under analysis is reported as having a void. The void location is approximately at depth of ½ Vs*tm, Vs being the sound velocity in copper.

As can be seen from the measured signal graphs (e.g., FIG. 5b), echo patterns can be characterized by a distinct characteristic frequency. Calculating periodograms on a part of a signal selected by a sliding time window, which is comparable (~2-3×) with the typical time duration of the echo, across the measured signal will produce a function F(t,w) equal the power density at frequency w from the periodogram obtained with the window centered around t. When the window covers the echo part of the signal, there will be peaks in the power spectrum corresponding to the echo characteristic frequencies. Location of the time window $t_m$, where these power densities are the strongest will correspond to the echo return time. Void location is approximately at depth of ½ Vs*$t_m$, Vs being the sound velocity in copper.

It should be appreciated that many alternative signal processing methods can be employed. For example, "Background subtraction" can also be employed. As one can see on the measured data graphs in FIGS. 15 and 16, substantially oscillatory acoustic response occurs on top of the slow decaying background signal. Prior to the echo pattern matching, this background can be subtracted by fitting to a polynomial or a linear combination of the decaying exponentials.

In addition, signal frequency filtering for "Echo Pattern matching" could be employed. As echo pattern has characteristic frequency distribution, it can be beneficial to run the measured signal via the frequency filter to suppress frequencies that are substantially higher and/or lower than the characteristic echo frequencies. This will make echo pattern matching more robust in case of the relatively high signal-to-noise ratio (SNR).

Many other alternative techniques are also contemplated as part of this disclosure, e.g., finite element method (FEM) or similar computer simulations can be performed ahead of the measurements for a given parameter of the via (e.g., diameter, depth, sidewall angle, liner or adhesion layers, etc.) and the "template" signal vector (TSV) determined from such simulations and saved as part of the recipe instead of clipping from the actual measurement.

Further analysis steps can be done as well, for example, characterize the detected voids. As discuss above, in the case of the Time-Periodogram Analysis, details of the spectral power density distribution for the return echo can be used to characterize void size and shape. This would require establishing correlations between the spectrum and void size and shape. These correlations can be established either with the FEM or similar simulations, or collecting measurements on the samples which are then analyzed by electron microscopy or other techniques capable to characterize void shape and size. It should be appreciated that the signals from the referenced measurements or simulations can be used to train and optimized the artificial neural network estimator to determine void characteristics from the production measurements.

Although specific embodiments of the present invention have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A method for nondestructively examining subsurface structures on semiconductor devices comprising:
   inducing at least an acoustic wave at a first location on an outer surface of a semiconductor device adjacent a structure that is at least partially embedded below the outer surface of the semiconductor device;
   detecting with a probe laser an effect of the induced acoustic wave at a second location on the outer surface of a semiconductor device, the structure being positioned at least partially between the first and second locations; and,
   measuring the time the acoustic wave takes to travel from the first location to the second location,
   repeating the inducing, detecting and measuring steps at a plurality of respective different first and different second positions relative to the structure to identify at least one characteristic of the structure.

2. The method of claim 1, wherein the detecting step includes using the probe laser to measure data representative of at least one of a physical distortion or index of refraction at the second location.

3. The method of claim 1, further comprising determining the frequency of the induced acoustic wave at the second location.

4. The method of claim 1, wherein the step of inducing at least an acoustic wave includes pulsing a pump laser for a first predetermined period of time.

5. The method of claim 4, wherein the first predetermined period of time is between one to one hundred nanoseconds.

6. The method of claim 1, wherein the characteristic of the structure that is identified is a position of the structure.

7. The method of claim 1, wherein the structure is selected from a group consisting of a via and a pillar and wherein the characteristic of the structure that is identified is selected from a group consisting of data regarding the existence of an abnormality and data regarding a dimension of interest.

8. The method of claim 1, wherein the detecting step occurs within a second predetermined time period that is based at least in part on expected position of the structure relative to the first and second locations.

9. The method of claim 8, wherein the detecting step occurs within a second predetermined time period which is determined at least in part by modeling how long the acoustic wave takes to travel between the first and second locations of the semiconductor substrate as a function of at least two characteristics selected from a group consisting of diameter, depth, shape, structure of the semiconductor substrate, material of the semiconductor substrate, stress in the substrate, position of the structure relative to the first and second positions, material in the structure, and shape of the structure.

\* \* \* \* \*